US00PP34125P2

(12) United States Plant Patent
Yencho et al.

(10) Patent No.: US PP34,125 P2
(45) Date of Patent: Apr. 12, 2022

(54) SWEETPOTATO PLANT NAMED 'NC04-0531'

(50) Latin Name: ***Ipomoea batatas* (L.) Lam.**
Varietal Denomination: NC04-0531

(71) Applicant: North Carolina State University, Raleigh, NC (US)

(72) Inventors: George Craig Yencho, Raleigh, NC (US); Kenneth Vincent Pecota, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 17/300,482

(22) Filed: Jul. 15, 2021

(51) Int. Cl.
*A01H 5/06* (2018.01)
*A01H 6/00* (2018.01)

(52) U.S. Cl.
USPC ..... Plt./258
CPC ..... *A01H 6/00* (2018.05)

(58) Field of Classification Search
USPC ..... Plt./258
CPC ..... A01H 5/06; A01H 5/12
See application file for complete search history.

(56) References Cited

PUBLICATIONS https://content.ces.ncsu.edu/north-carolina-organic-commodities-production-guide/chapter-8-crop-production-management-sweetpotatoes; Jun. 24, 2019; 11 pages.*

* cited by examiner

*Primary Examiner* — Kent L Bell
(74) *Attorney, Agent, or Firm* — Myers Bigel, P.A.

(57) ABSTRACT

*Ipomoea batatas* 'NC04-0531' is an orange fleshed, smooth skinned, dark rose-colored, table stock sweetpotato. 'NC04-0531' has good insect resistance. It has an upright, compact canopy that helps to suppress weeds within a row and is slower to trail across rows allowing for a longer period of cultivation with weed control. It is a long season variety to size for optimal production of No. 1 sized roots. Size and shape uniformity of 'NC04-0531' are very good. The flavor of the baked storage roots of 'NC04-0531' has been judged to be very good by standardized and informal taste panels. Because of its insect resistance and plant canopy characteristics, 'NC04-0531' is seen as a good option for organic production.

7 Drawing Sheets

Latin name of the genus and species: The Latin name of the novel plant cultivar disclosed herein is *Ipomoea batatas* (L.) Lam.

Variety denomination: This new and distinct sweetpotato cultivar of *Ipomoea batatas* (L.) Lam. has been given the denomination 'NC04-0531'.

BACKGROUND OF THE INVENTION

*Ipomoea batatas* is a member of the morning glory family Convolvulaceae. This species is grown worldwide, and it exhibits a wide range of plant forms and colors. Grown by farmers worldwide, the cultivated members of *Ipomoea batatas* are commonly produced for consumption of their nutritious, enlarged storage roots. This contrasts with potatoes (*Solanum tuberosum*), which produce an edible tuber derived from an underground stem, which is similar in structure to the above ground stems.

Presently, there are two dominant sweetpotato cultivars produced in the United States, 'Covington' (U.S. Plant Pat. No. 18,516) and 'Beauregard' (unpatented). 'NC04-0531' provides an improvement over 'Covington' and 'Beauregard' in that it has increased resistance to insect damage, and a canopy that is more upright and has a less trailing plant habit allowing for a longer mechanical cultivation period for weed control. 'NC04-0531' provides an improvement over 'Beauregard' in consistency of storage root shape attributes.

Lineage. 'NC04-0531' originated from bulked botanical seed harvested from the open pollinated female parent 'Ruddy' (not patented) in the 2003 Elite polycross nursery. The 2003 Elite breeding nursery was planted in Clayton, Johnson County, N.C. The 15 genotypes present in the Elite nursery were randomly mated during the course of a five-month flowering period in which seed was harvested and bulked per female parent from the 15 genotypes present in the nursery; therefore, the male parent of 'NC04-0531' is unknown. Two patented male parents ('L96-117' (U.S. Plant Pat. No. 15,038) and 'Bienville' (U.S. Plant Pat. No. 15,380)) were in the nursery and these represent potential pollen sources.

Seedlings from the 2003 Elite polycross nursery were planted in Clinton, N.C. greenhouses in March of 2004. A single cutting was taken from each seedling and planted in the field on May 22$^{nd}$ in Kinston N.C. and 'NC04-0531' was selected as a "single plant selection" on September 13$^{th}$. This "single plant selection" included all of the storage roots derived from the single plant cutting planted on May 23$^{rd}$, typically 2-15 storage roots, with 2-10 storage roots being saved over the winter in our storage facility in Clinton, N.C. for propagation the next year via vegetive propagation in the same location.

Asexual Reproduction. The first asexual reproduction of 'NC04-0531' occurred in Clinton, N.C. 'NC04-0531' has been propagated as vegetative stem cuttings and/or storage root derived stem cuttings derived from adventitious sprouts emanating from its storage roots since its original selection in September of 2004. After further cycles of selection for horticultural traits and disease screenings, 'NC04-0531' was subjected to meristem tip culture and subsequent tissue culture maintenance to eliminate viruses and pathogens via meristem tip culture. The characteristics disclosed herein for 'NC04-0531' have remained stable and the plant has reproduced true to type through successive generations of asexual propagation.

SUMMARY OF THE INVENTION

'NC04-0531' is an orange-fleshed, smooth-skinned, dark rose-colored table stock sweetpotato. The storage roots of 'NC04-0531' tend to be elliptic and similar in length to 'Covington' but shorter than 'Beauregard', and more uniform in size and shape than 'Beauregard'. One of the desirable traits of 'NC04-0531' is that it produces more consistent storage root shapes than 'Beauregard', especially in soils where 'Beauregard' can be long and irregular. The length of the storage roots of 'NC04-0531' are similar to 'Covington' and shorter than 'Beauregard'. 'NC04-0531' produces a similar percentage of No. 1 storage roots to 'Covington'. 'NC04-0531' is a later maturity clone and does not yield as high as 'Covington' and 'Beauregard', when these three clones are harvested at the same time. Plants from bedded storage roots of 'NC04-0531' are ready 10 days to two weeks before 'Covington'. 'NC04-0531' has been rated more resistant to insect damage than 'Covington' and 'Beauregard', and has a compact, upright growth habit that allows for a longer cultivation period than 'Covington' and 'Beauregard' without damaging the vines. The insect resistance and longer cultivation period make 'NC04-0531' an attractive option for organic producers. The dry matter content is higher for 'NC04-0531' than for 'Covington' and 'Beauregard'. The flavor of baked storage roots of 'NC04-0531' have been judged to be very good by standardized and informal taste panels. 'NC04-0531' typically scores as well as or better than 'Covington' and 'Beauregard' for baking quality. The female parent line, 'Ruddy', was no longer propagated at the time that 'NC04-0531' was being evaluated. So, with the exception of insect resistance, 'Ruddy' was not used for comparison. 'Ruddy' is not grown commercially.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION

The following is a detailed description of the botanical characteristics of a new and distinct cultivar of *Ipomoea batatas* plant given the designation 'NC04-0531'. All colors cited herein refer to The Royal Horticulture Society Colour Chart designations (The Royal Horticultural Society, London, 1995, $4^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134pp.). Where dimensions, sizes, colors, and other characteristics are given, it is to be understood that such characteristics are approximations or averages set forth as accurately as practicable.

The descriptions and measurements of plant canopy reported herein were done on field grown plants 57 days after planting (DAP). The plants were grown in Kinston, N.C. under common commercial sweetpotato production practices during June through October. 'NC04-0531' has not been observed under all possible environmental conditions; therefore, the phenotype may vary under different environmental conditions such as season, temperature, light intensity, day length, cultural conditions, and the like, without however, any variance in the genotype.

The following discussion provides a description of the new *Ipomoea batatas* 'NC04-0531' with 'Beauregard' and 'Covington' for comparison.

Classification:

*Botanical name.*—*Ipomoea batatas* (L.) Lam.

*Common name.*—Sweetpotato.

*Variety name.*—'NC04-0531'.

Figure 1:
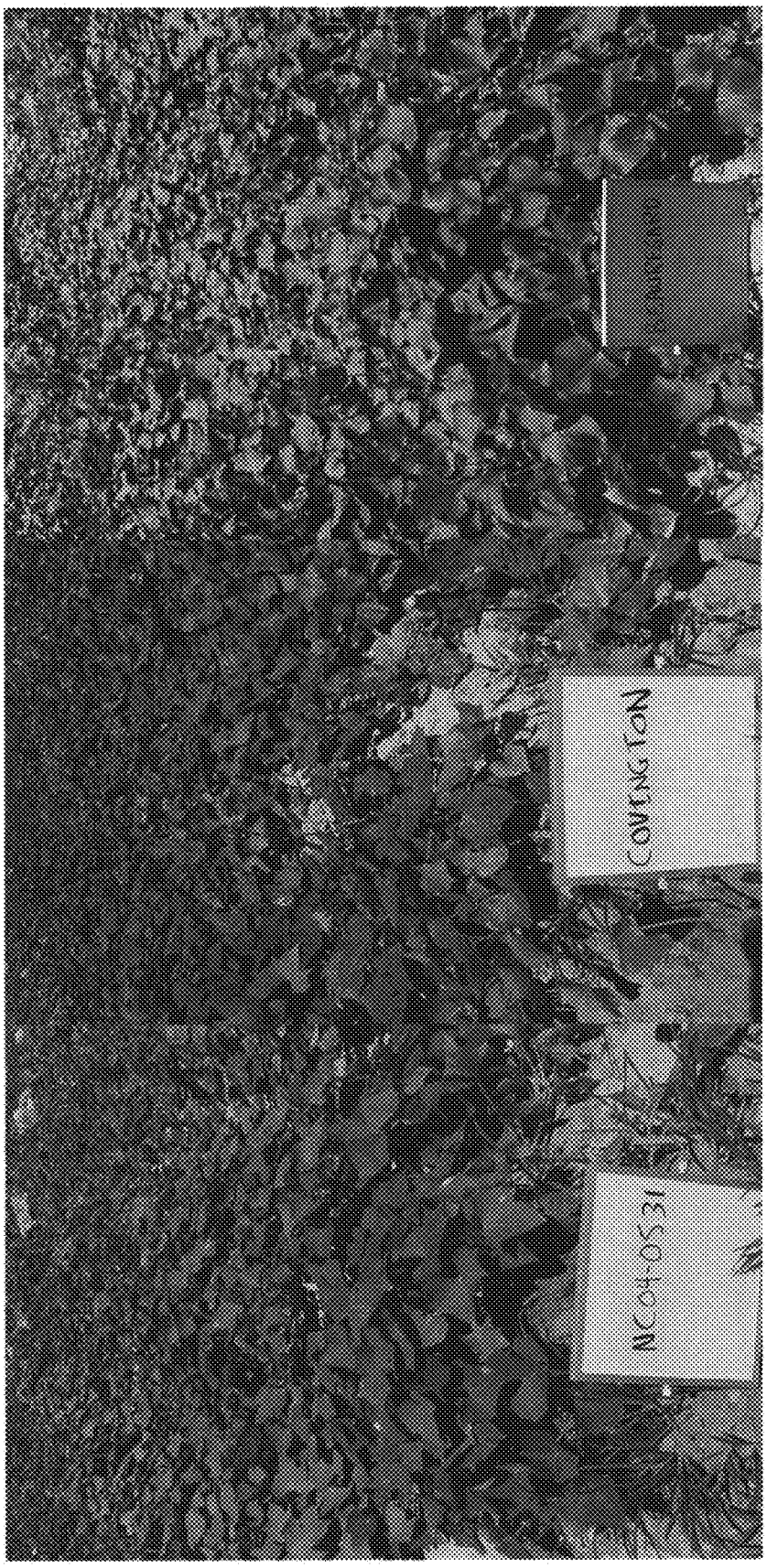
FIG. 1 is a color photograph of the above ground plant canopy produced by the new cultivar 'NC04-0531' (left panel), 'Covington' (middle panel) and 'Beauregard' (right panel) 57 days after planting at in Kinston, N.C. in 2017.

Growth Conditions Whole-plant Canopy Structure. FIG. 1 is a color photograph of the canopy biomass produced by the new cultivar 'NC04-0531' and contrasted with 'Covington' and 'Beauregard'. Measurements were collected on field-grown plants at 57 DAP using 20 measurements per trait and recorded as the mean. 'NC04-0531' averaged 1.4 main vines and 'Covington' and 'Beauregard' each averaged 1.1 main vines. Mean main vine lengths were 66, 179, and 136 cm for 'NC04-0531', 'Covington', and 'Beauregard', respectively. The mean main vine stem diameter at the base was 8.2, 8.1, and 8.4 mm ('NC04-0531', 'Covington', and 'Beauregard', respectively). At 50 cm from the base of the main vine, the mean stem diameter was 6.2, 4.9, and 4.8 mm for 'NC04-0531', 'Covington', and 'Beauregard', respectively. The average lateral branches per main vine was 5.3 for 'NC04-0531', 4.5 for 'Covington', and 5.9 for 'Beauregard'. Stem color was green (N144B to 144B) for 'NC04-0531', 145A for 'Covington', and 144B for 'Beauregard'. The first internode length beginning at the apex between the first and second fully expanded leaves was 30 mm for 'NC04-0531', 52 mm for 'Covington', and 56 mm for 'Beauregard'. 'NC04-0531' appeared to have a denser canopy and greater ground cover for potential weed suppression ability within the rows when compared to 'Covington' and 'Beauregard'.

Figure 2A:
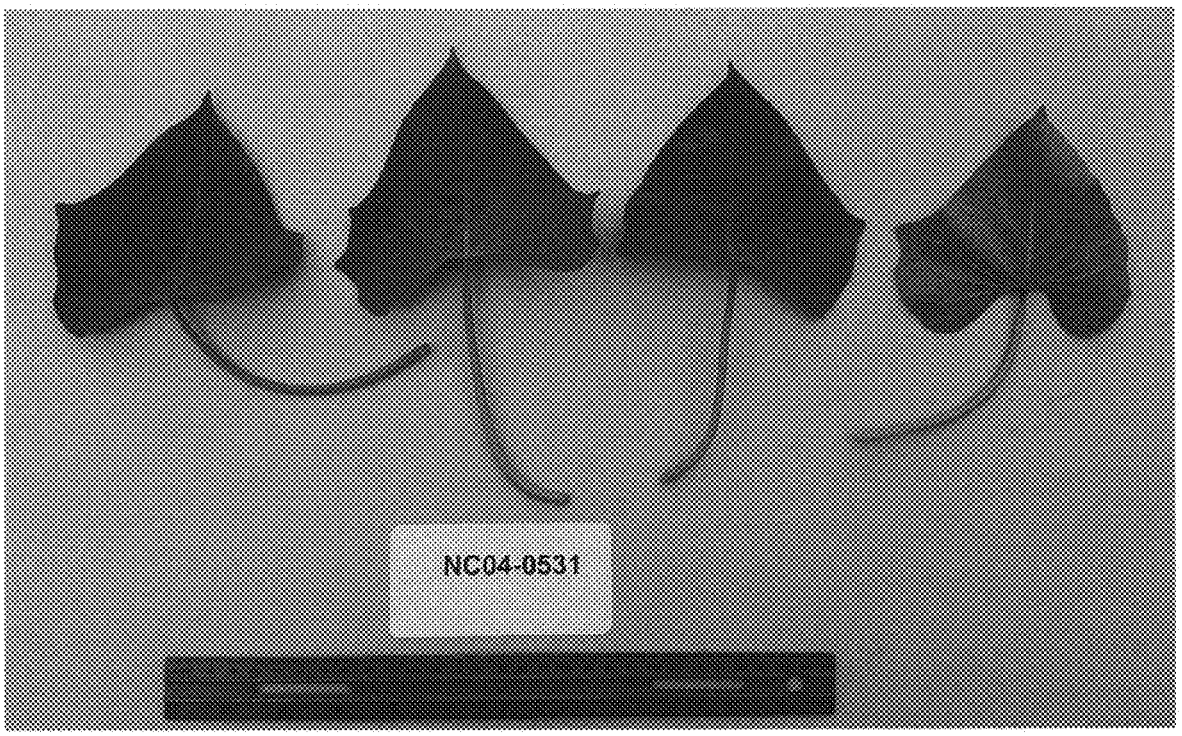
FIGS. 2A-2C are color photographs of typical mature leaves of 'NC04-0531' (FIG. 2A), 'Covington' (FIG. 2B), and 'Beauregard' (FIG. 2C) 57 days after planting in Kinston, N.C. in 2017.
Figure 2B:
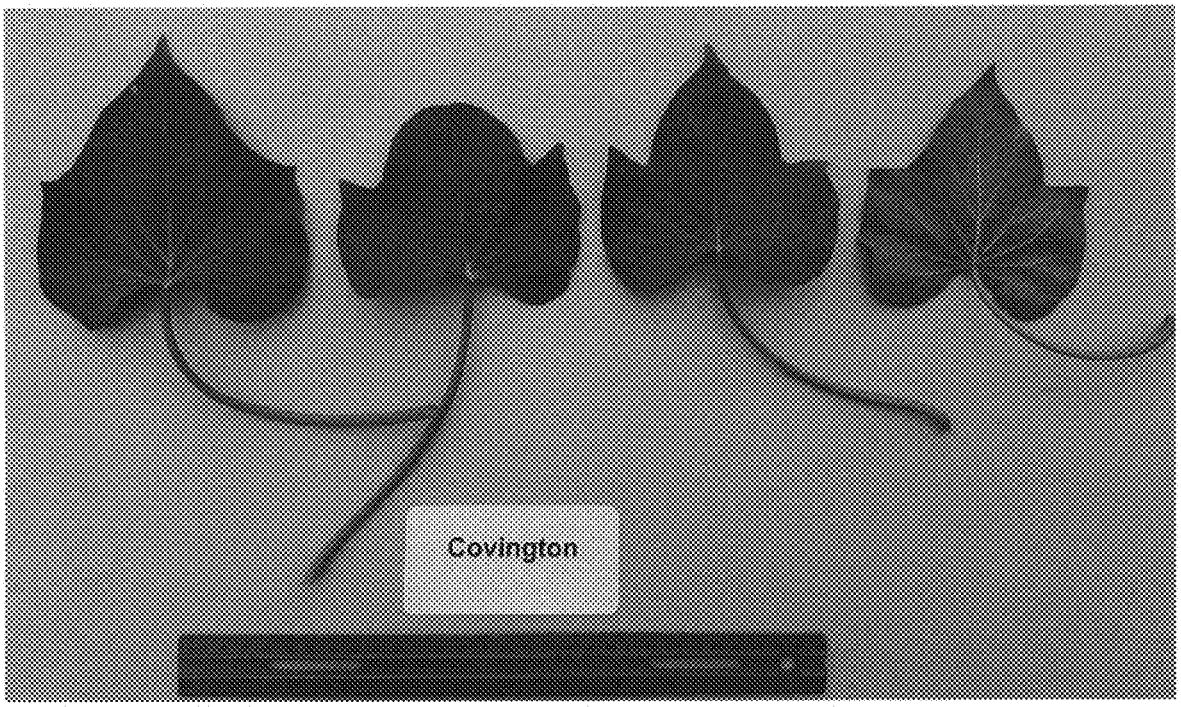
Figure 2C:
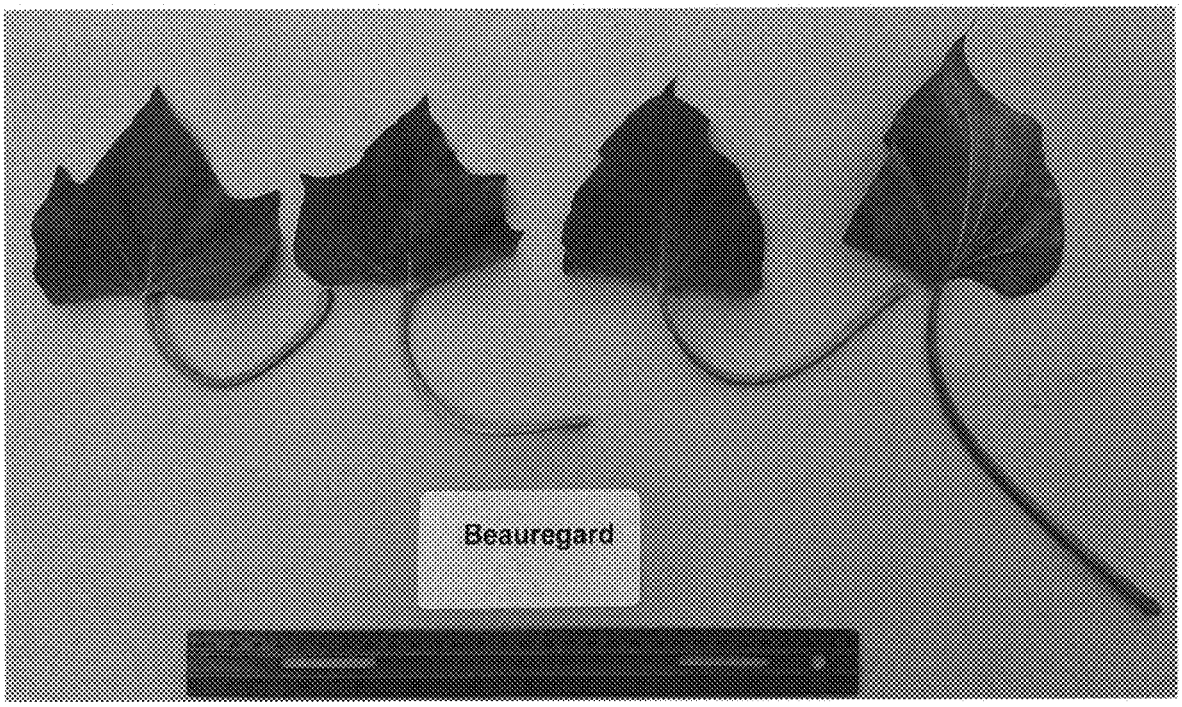
Figure 3A:
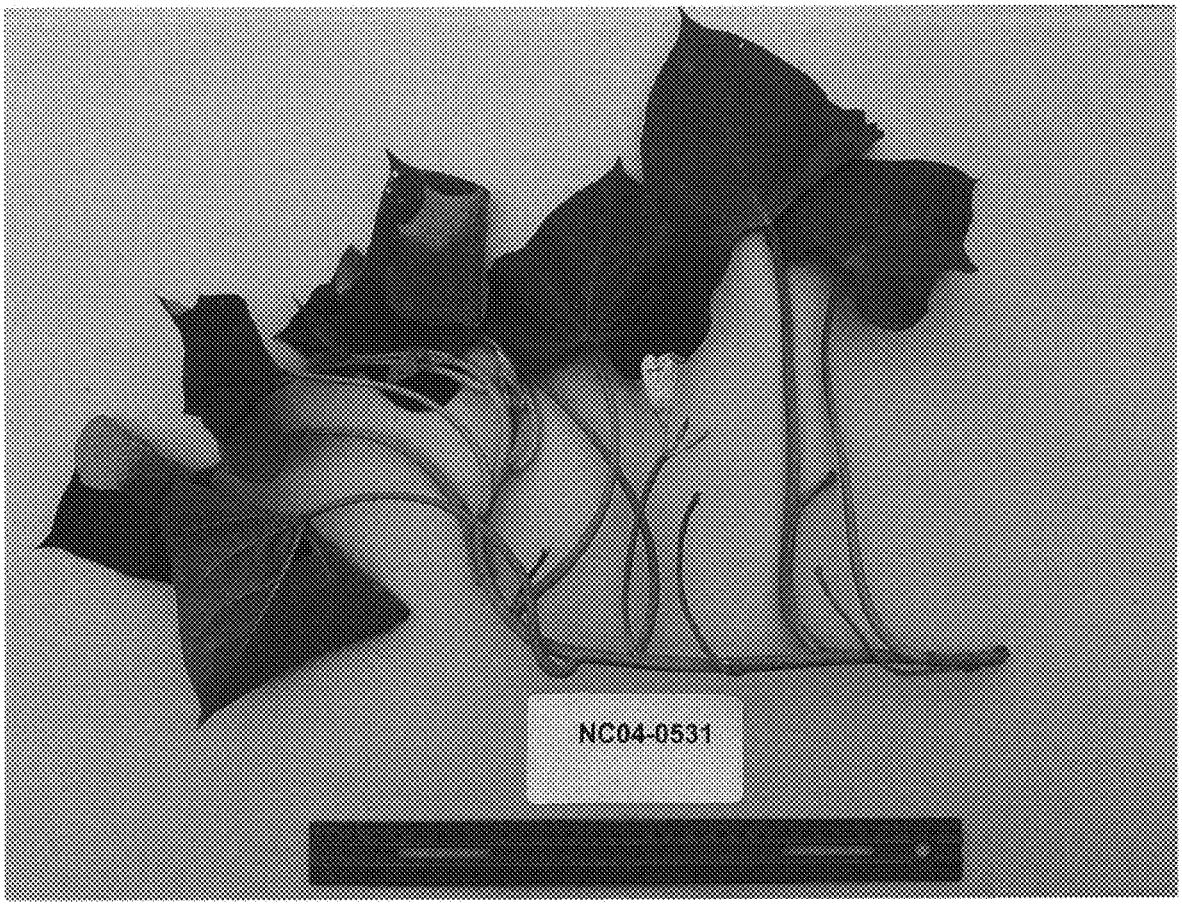
FIGS. 3A-3C are color photographs showing typical vines and the variety of leaves of 'NC04-0531' (FIG. 3A), 'Covington' (FIG. 3B), and 'Beauregard' (FIG. 3C) 57 days after planting in Kinston, N.C. in 2017.
Figure 3B:
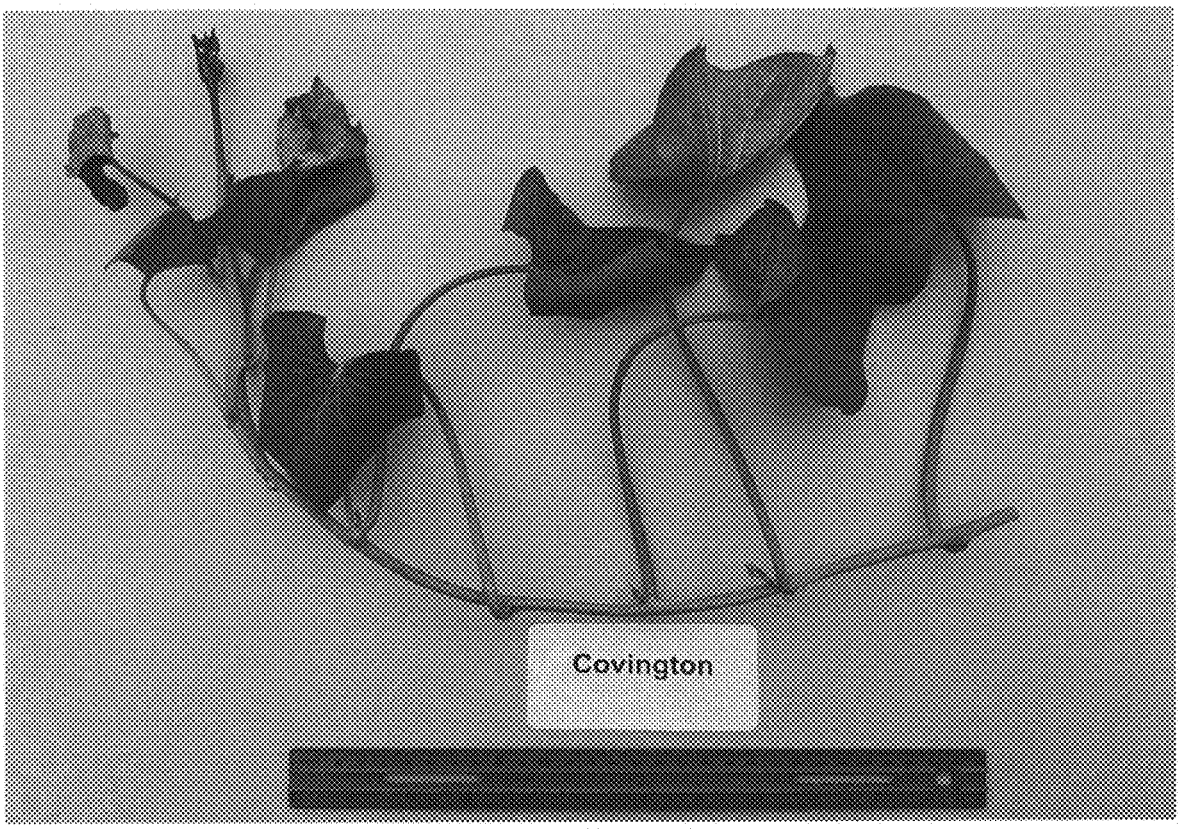
Figure 3C:
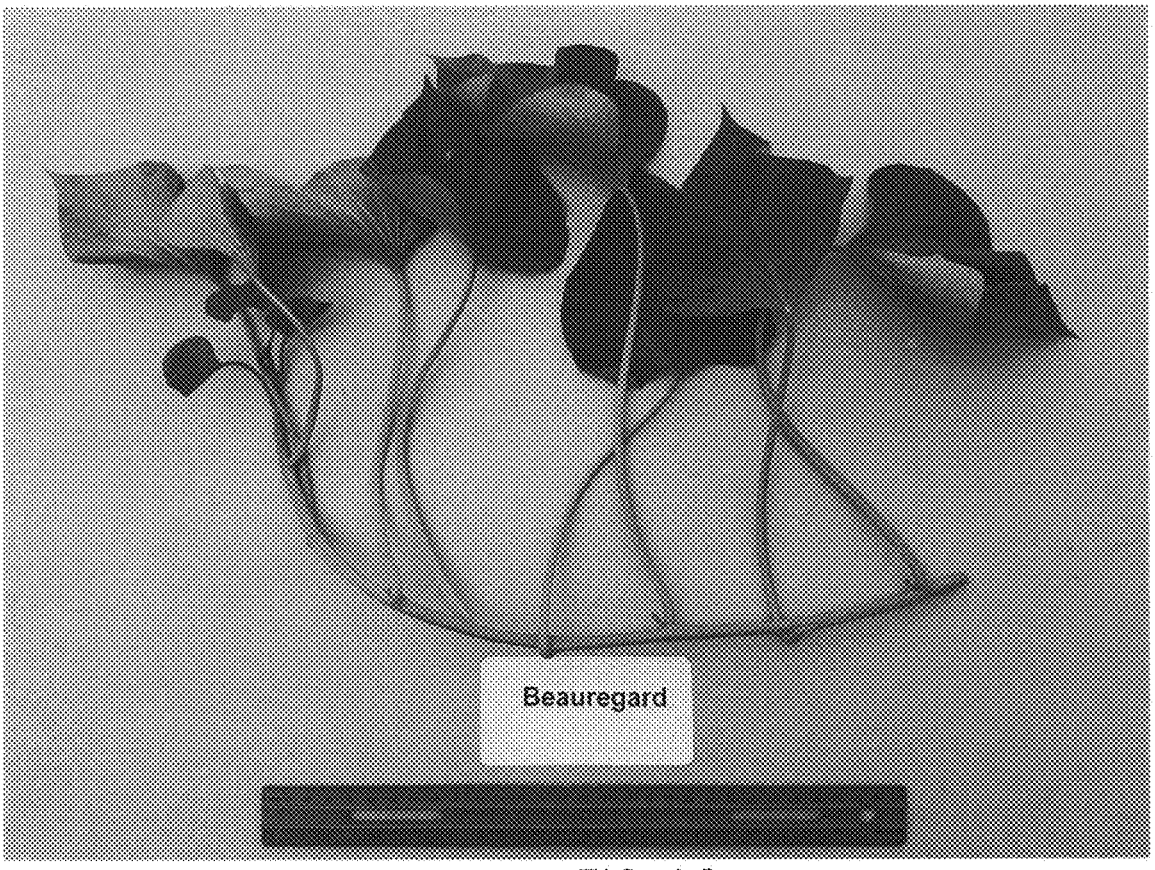

Foliage. The leaves of 'NC04-0531' are alternate and simple in structure, and cordate to very slightly lobed in shape. (FIGS. 2A and 3A). The leaves have a smooth texture and matte finish. Mature leaf color for 'NC04-0531', 'Covington', and 'Beauregard' is green, between 147A and 147B on the upper leaf surface and 147B on the lower surface. Young leaf color, upper and lower, displayed variation among the three cultivars; 'NC04-0531' was green between 146A to 146B, 'Covington' was green 147B with secondary purple base (N79A), and 'Beauregard' was green 147A with secondary purple (N79B), however slightly less purple pigmentation than 'Covington'. Mean leaf length was 122 mm for 'NC04-0531', 119 mm for 'Covington' and 114 mm for 'Beauregard. Leaf width was 145 mm for 'NC04-0531', 134 mm for 'Covington', and 119 mm for 'Beauregard'. All three cultivars have a purple spot (N79B) spot at the base of the main rib. Petioles of 'NC04-0531' are green (144C) with purple near leaf blade (N79A), and green (144B) for both 'Covington' and 'Beauregard' with no secondary color. Mean petiole length and diameter measured 205 mm and 5.8 mm for 'NC04-0531', 181 mm and 5 mm for 'Covington', and 158 mm and 4.5 mm for 'Beauregard'. Stem tip anthocyanin coloration of 'NC04-0531' is absent with sparse pubescence.

A typical inflorescence of 'NC04-0531' has two clusters of 6-10 flowers per peduncle. Peduncles are green (144A) averaging 12 cm long and about 3.5 mm in diameter. Flowers are 3.5 to 4 cm long from the base of the calyx, and the corolla is 4 to 4.5 cm wide. Petals are fused to form a pentagonal limb with smooth edges. The inner throat color is purple (N81A) with a white inner and outer limb. Upper and lower flower texture is smooth. The five sepals making up the calyx were elliptic with an acute tip. The three inner sepals were 12 mm long and 5.4 mm wide while the outer two sepals were shorter, 10.5 mm long and 3.3 mm wide. All sepals were green (144A) with smooth edges. The pistil averages 16 mm in length and are white and the stigma is slightly inserted. Anthers are white with the style being white with purple at the base (76A). No fragrance is present.

Figure 4:
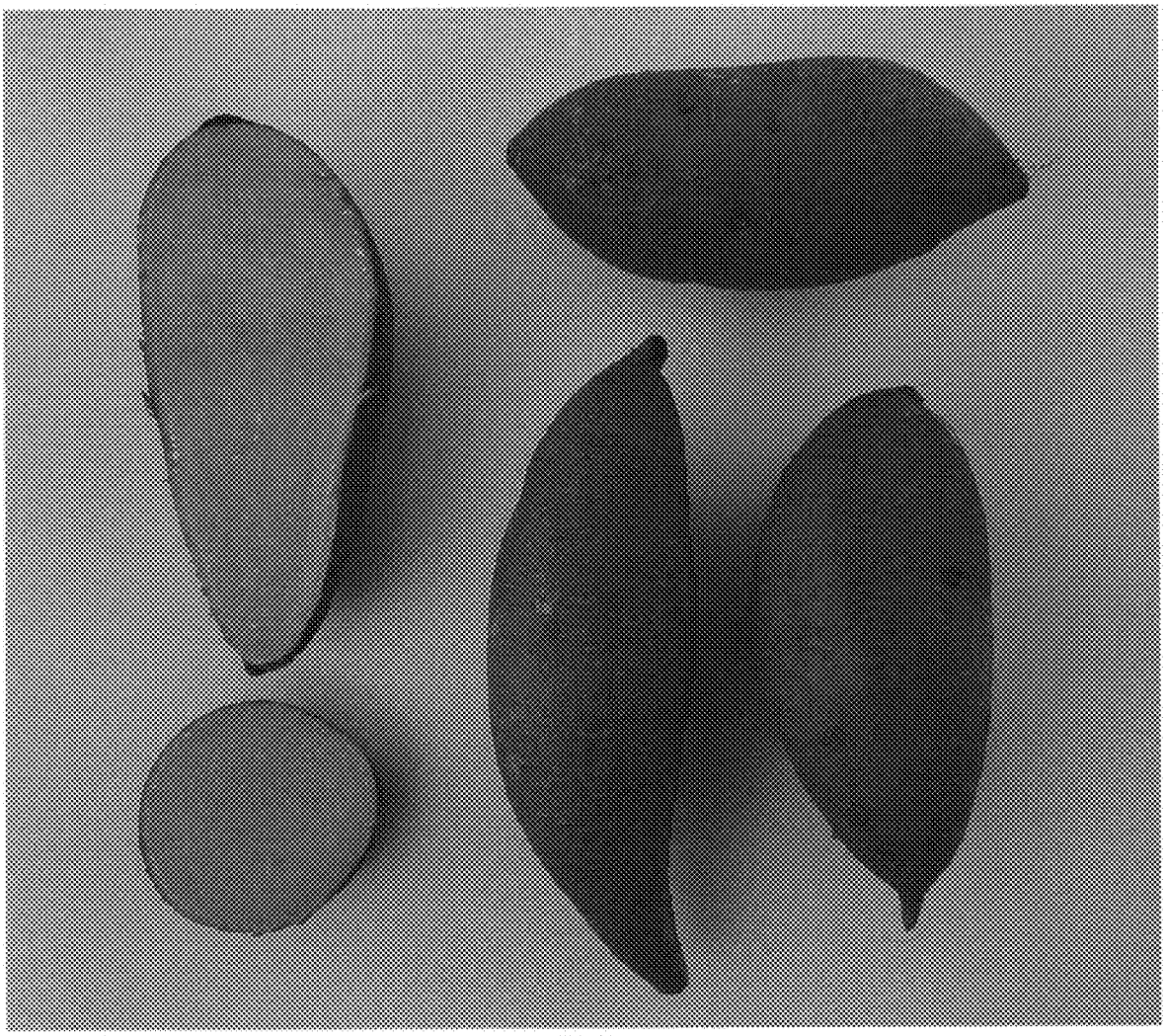
FIG. 4 is a color photograph showing typical storage roots produced by 'NC04-0531'. The photographs were taken of storage roots that had been stored in a sweetpotato storage facility for approximately three months after harvest.

Storage Roots. 'NC04-0531' produces orange fleshed (between 28B and 29A), smooth skinned, storage roots that are generally elliptic. The skin color of 'NC04-0531' is dark rose (178B to N181A) (FIG. 4), which is typically darker and redder than 'Covington' when grown under similar conditions. One of the additional desirable attributes of 'NC04-0531' is that it produces roots that are shorter than 'Beauregard' for soils and conditions where 'Beauregard' can be long. Roots of 'NC04-0531' are generally similar in length to 'Covington' and shorter in length to 'Beauregard'. Length to diameter ratios of storage roots in 26 trials over seven years averaged 2.4, 2.6 and 2.0 for 'NC04-0531', 'Beauregard' and 'Covington' respectively. Root number and size was measured for 11 trials in 2017 and 2018 with 'NC04-0531' averaging 3.3 roots per plant while 'Beauregard' averaged 4.9 and 'Covington' 4.1 roots per plant. Mean length of the roots for 'NC04-0531' was 4.4 inches and mean width 2.3 inches. For 'Beauregard', mean length of the roots was 5.0 inches with a mean width of 2.4 inches, and for 'Covington' mean length of the roots for was 4.6 inches with a mean width of 2.4 inches. Carbohydrate profiles and β carotene levels are similar to 'Beauregard' and 'Covington', with all three being moist, sweet, orange-fleshed types (Table 1). Percent dry matter and starch content is slightly higher for 'NC04-0531' than both 'Beauregard' and 'Covington', but not different enough to change cooking quality. The flavor of the baked storage roots of 'NC04-0531' have been judged to be very good by standardized and informal taste panels comparing well with 'Covington'.

TABLE 1

Carbohydrate, n-carotene and asparagine profiles of 'NC04-0531', 'Beauregard' and 'Covington' from the same trials averaged over 5 trials in 2014, 6 in 2015, 4 in 2016 and 10 trials in 2017.

| Cultivar | % dry matter | Starch g/100 g dry weight | Fructose g/100 g fresh weight | Glucose g/100 g fresh weight |
|---|---|---|---|---|
| | | 2014 | | |
| 'N004-0531' | 23.6 ± .6 | 53.2 ± 2.4 | 0.39 ± .03 | 0.50 ± .05 |
| 'Beauregard' | 19.3 ± .2 | 49.3 ± 0.9 | 0.77 ± .04 | 1.03 ± .06 |
| 'Covington' | 20.9 ± .7 | 42.2 ± 2.1 | 0.58 ± .06 | 0.75 ± .09 |
| | | 2015 | | |
| 'NC04-0531' | 23.8 ± .3 | 55.5 ± 1.5 | 0.35 ± .01 | 0.43 ± .02 |
| 'Beauregard' | 18.5 ± 1.5 | 44.5 ± 4.0 | 0.70 ± .10 | 0.94 ± .14 |
| 'Covington' | 21.0 ± .8 | 44.8 ± 1.9 | 0.45 ± .06 | 0.56 ± .08 |
| | | 2016 | | |
| 'NC04-0531' | 23.3 ± .7 | 48.4 ± 3.0 | 0.36 ± .05 | 0.48 ± .10 |
| 'Beauregard' | 19.8 ± .6 | 47.9 ± 1.2 | 0.77 ± .07 | 1.01 ± .11 |
| 'Covington' | 21.4 ± .6 | 42.8 ± 3.5 | 0.41 ± .06 | 0.52 ± .10 |
| | | 2017 | | |
| 'NC04-0531' | 23.9 ± .4 | 53.0 ± 1.1 | 0.37 ± .02 | 0.46 ± .03 |
| 'Beauregard' | 21.2 ± .4 | 53.0 ± 1.2 | 0.67 ± .04 | 0.88 ± .06 |
| 'Covington' | 22.4 ± .5 | 46.9 ± 1.6 | 0.41 ± .02 | 0.50 ± .02 |

| Cultivar | Sucrose g/100 g fresh weight | Total sugars g/100 g fresh weight | β-carotene mg/g dry wt | Asparagine mg/g dry wt |
|---|---|---|---|---|
| | | 2014 | | |
| 'N004-0531' | 2.22 ± .19 | 3.11 ± .27 | 0.46 ± .02 | 0.96 ± .20 |
| 'Beauregard' | 1.10 ± .06 | 2.89 ± .11 | 0.46 ± .01 | 1.20 ± .32 |
| 'Covington' | 2.63 ± .07 | 3.96 ± .19 | 0.55 ± .02 | 0.91 ± .15 |
| | | 2015 | | |
| 'NC04-0531' | 1.87 ± .11 | 2.65 ± .10 | 0.40 ± .01 | 1.33 ± .23 |
| 'Beauregard' | 0.89 ± .12 | 2.52 ± .25 | 0.41 ± .02 | 2.24 ± .39 |
| 'Covington' | 2.19 ± .11 | 3.20 ± .13 | 0.48 ± .02 | 1.68 ± .22 |
| | | 2016 | | |
| 'NC04-0531' | 2.30 ± .19 | 3.14 ± .30 | 0.46 ± .06 | 1.12 ± .19 |
| 'Beauregard' | 0.98 ± .09 | 2.76 ± .25 | 0.40 ± .02 | 1.26 ± .12 |
| 'Covington' | 2.68 ± .29 | 3.61 ± .41 | 0.51 ± .05 | 0.92 ± .22 |
| | | 2017 | | |
| 'NC04-0531' | 2.33 ± .08 | 3.17 ± .10 | 0.44 ± .03 | 1.04 ± .14 |
| 'Beauregard' | 1.20 ± .04 | 2.75 ± .10 | 0.40 ± .02 | 1.24 ± .17 |
| 'Covington' | 2.59 ± .13 | 3.50 ± .15 | 0.54 ± .02 | 0.91 ± .12 |

Values are based on predictions using Near Infrared Reflectance Spectroscopy (NIRS) calibrations.
Samples are measured 4-10 weeks after harvest.
Values are means with standard errors.

Storage Root Yield. Yield comparisons of 'NC04-0531' are with 'Covington' and 'Beauregard', the two major sweetpotato cultivars grown in the U.S. In the 30 replicated yield trials comparing 'NC04-0531', 'Beauregard' and 'Covington', 'NC04-0531' averaged 85% of the total marketable yield (TMY) of 'Beauregard' and 81% the TMY of 'Covington' (Table.2). While the yields in these trials were lower for 'NC04-0531', the timing for these trials were based on optimal sizing for No. 1 sized roots for the check cultivars, 'Beauregard' and 'Covington'. 'NC04-0531' does not bulk as quickly as the check cultivars and would normally be left to grow for 2-4 weeks longer to optimize production of No. 1 sized roots. 'Beauregard' and 'Covington' are typically harvested between 100-120 days after planting, while recommendations for 'NC04-0531' are 115-140 days. Yields are closer to the 'Beauregard' and 'Covington' when following these guidelines, which guidelines are common for later sizing cultivars. Production of off shaped roots, which if severe would be culled, is similar to 'Covington' and less than 'Beauregard'.

TABLE 2

Average performance of 'NC04-0531', 'Covington' G2* and B94-14 G2* 'Beauregard' over 30 yield tests, 2007-2017.

| | Total | Marketable Yield | | | Size Distribution by Class (% of total yield) | | | | No. 1 50 |
|---|---|---|---|---|---|---|---|---|---|
| Cultivar | Yield bu/A | bu/A | % Beau | % Cov | No. 1 | Can | Jumbo | Cull | lb bu/ac |
| 'NC04-0531' | 698 | 663 | 85 | 81 | 57 | 27 | 11 | 5 | 378 |
| 'Covington' G2 | 909 | 850 | 108 | | 58 | 16 | 20 | 6 | 493 |
| 'Beauregard' G2-3 (B94-14) | 965 | 842 | | 102 | 47 | 14 | 26 | 13 | 396 |

*G2 - Field generation designation of the planting materials used in the trials

US #1's - Roots 2" to 3½" diameter, length of 3" to 9", must be well shaped and free of defects.

Canners - Roots 1" to 2" diameter, 2" to 7" in length.

Jumbos - Roots that exceed the diameter, length and weight requirements of the above two grades, but are of marketable quality.

Percent US #1's - Calculated by dividing the weight of US #1's by the total marketable weight (Culls not included).

Culls - Roots must be 1" or larger in diameter and so misshapen or unattractive that they could not fit as marketable roots in any of the above three grades.

Insect Resistance. 'NC04-0531' has good resistance to the WDS (wireworm, *Diabrotica, Systena*) complex of insects, which are the major causes of insect damage of sweetpotato in North Carolina, compared to the major cultivars 'Beauregard' and 'Covington'. The results of four replicated field insect screen trials are shown in Table 3. WDS resistance is similar to slightly less than 'Ruddy' which is used as an insect resistant check and is the parent of 'NC04-0531'. Sweetpotato flea beetle (*Chaetocnema confinis* Crotch) and sweetpotato weevil (*Cylas formicarius* (F.) damage were too low in these trials to assess resistance.

TABLE 3

Insect resistance screens with 'NC04-0531', 'Beauregard', 'Covington' and 'Ruddy' sweetpotatoes in four replicated trials.

| Sweetpotato genotype | Uninjured roots, % | WDS[1] severity index | SPFB[2] damaged roots, % | SPW[3] damaged roots, % |
|---|---|---|---|---|
| 2012 USDA-US Vegetable Lab Advanced trial evaluation | | | | |
| 'Ruddy'[b] | 95 a | .03 b | 1.8 b | 0 a |
| 'NC04-0531' | 69.5 b | .25 b | 10.6 ab | 2.1 a |
| 'Covington' | 38.8 c | .69 a | 7.4 ab | 7.3 a |
| 'Beauregard'[c] | 29 c | .84 a | 14.8 a | 5.3 a |
| 2012 USDA-US Vegetable Lab Insect trial evaluation | | | | |
| 'Ruddy' | 99.2 | 0.000 | 0.01 | 0 |
| 'NC04-0531' | 87.5 | 0.095 | 0.03 | 0.02 |
| 'Covington' | 73.4 | 0.255 | 0.02 | 0.01 |
| 'Beauregard' | 73.0 | 0.253 | 0.05 | 0 |

TABLE 3-continued

Insect resistance screens with 'NC04-0531', 'Beauregard', 'Covington' and 'Ruddy' sweetpotatoes in four replicated trials.

| Sweetpotato genotype | Uninjured roots, % | WDS[1] severity index | SPFB[2] damaged roots, % | SPW[3] damaged roots, % |
|---|---|---|---|---|
| 2011 USDA-US Vegetable Lab Insect trial evaluation | | | | |
| 'Ruddy' | 87.3 | 0.120 | 0 | 0 |
| 'NC04-0531' | 85.7 | 0.105 | 0.03 | 0 |
| 'Covington' | 34.5 | 0.737 | 0.05 | 0.003 |
| 'Beauregard' | 21.1 | 1.155 | 0.02 | 0.003 |
| 2007 NCSU insect resistance trials | | | | |
| 'NC04-0531' | 20.4 a | 1.10 b | 1.0 b | NA |
| 'Covington' | 21.3 a | 1.17 b | 2.0 b | NA |
| 'Beauregard' | 7.3 b | 1.74 a | 12.6 a | NA |

[1]Wireworm, Diabrofica, Systena (WDS) complex: severity index: 1 = 1-5 scars, 2 = 6-10 scars, 4_10 scars, averaged over all roots; maximum score = 4.

[2]Sweetpotato Flea beetle (SPFB) damage - *Chaetocnema confinis* Crotch

[3]Sweetpotato Weevil (SPW) damage - *Cylas formicarius* (F.)

'Ruddy' is the resistant check for WDS, 'Beauregard' is the susceptible check.

Means within columns followed by a common letter are not significantly different (P = 0.05, Fisher's Least Significant Difference).

Disease or Pest Resistance. Table 4 summarizes the results of disease evaluations of 'NC04-0531'. Based on multiyear disease evaluations, 'NC04-0531' is resistant to Fusarium wilt (*Fusarium oxysporum* Schlect. f. sp. *batatas* (Wollenw.) Snyd. & Hans.), Streptomyces soil rot (*Streptomyces ipomoeae* (Person & W. J. Martin) Waksman & Henrici) and to southern root knot nematode, *Melodogyne incognita* (Kofoid & White). The *Fusarium* resistance of 'NC04-0531' is similar to 'Covington', which is important since there is no cultural control.

TABLE 4

Disease screen results for 'NC04-0531', 'Beauregard' and 'Covington' over five years for Southern root-knot nematode (*Meloidogyne incognita*) (Kofoid & White), *fusarium* wilt (*Fusarium oxysporum* Schlect. f sp. *batatas* (Wollenw.) Snyd. & Hans.), and Streptomyces soil rot (*Streptomyces ipomoeae* (Person & W. J. Martin) Waksman & Henrici)

| | 2014 | 2009 | 2008 | 2007 | 2006 | Average |
|---|---|---|---|---|---|---|
| 'NC04-0531' | | | | | | |
| Root-knot nematode | R | HR | R | R | MR | R |
| *Fusarium* wilt | R | R | R | R | HR | R |
| SSR - GH | MS | R | R | R | — | MR-R |
| SSR - field | R | R | R | R | R | R |
| 'Covington' | | | | | | |
| Root-knot nematode | R | R | R | R | MR | R |
| *Fusarium* wilt | R | R | R | R | R | R |
| SSR - GH | MR | R | R | R | R | R |
| SSR - field | R | R | R | R | R | R |
| 'Beauregard' | | | | | | |
| Root-knot nematode | HS | HS | HS | S | HS | HS |
| *Fusarium* wilt | MR | MR | R | R | R | MR-R |
| SSR - GH | R | R | R | R | — | R |
| SSR - field | R | R | R | R | R | R |

Scale - HS - highly susceptible, S - susceptible, MS - moderately susceptible, MR - moderately resistant, R - resistant, HR - highly resistant In Table 4, the root knot nematode rating is based on the number of galls on roots counted eight weeks after inoculation with 10,000 eggs of *M. incognita* race 3 in plants established in four-inch pots. Gall count classes: HR=0; R=1-3; MR=4-10; MS=11-30; S=31-100; HS=101+galls. 4 reps. The Fusarium wilt rating involves dipping fresh cut plants in a solution of *Fusarium oxysporum* spores then rating for mortality and vascular tissue browning. 3 reps of five plants each are used. *Streptomyces* soil rot is screened in both the greenhouse and field. The greenhouse trial involves planting slips into media that is a mix of sand and vermiculite media on which the bacteria is raised. Rating on damage to fibrous roots is done 8-10 weeks after planting. The field trial is in a field with high levels of SSR pressure. Plots are rated for both fibrous root damage, yield and storage root lesions Long term storage. Sweetpotatoes from yield trials are stored and rated for the ability to last until the next crop season. They are rated on a visual pithiness scale from 0 to 4, where 0 has visible holes, to 4, where there is no visible pithiness, or they look like freshly harvested roots. This rating system is used as an estimate of how well the roots have lasted in storage. The sweetpotatoes are also rated for sprouting, another measure of long-term storage, which is also reflected in the pithiness score. 'NC04-0531' had an average pithiness score of 2.9 averaged over 13 trials from 2012 to 2018. In the same years, the pithiness score for 'Covington' averaged 2.4 and 2.3 for 'Beauregard', both of these ratings are considered good for storage ability. So, we would also consider 'NC04-0531' to be good. Sprouting for 'NC04-0531' was minimal, similar to 'Covington' and 'Beauregard'.

'NC04-0531' is a fairly prolific producer of latex, which when the roots are broken off during harvest may exude from the root and run down the side of the sweetpotato. When the latex dries it turns black which is considered a visual defect. It does not come off in the packing process Flood tolerance appears to be slightly less for 'NC04-0531' than 'Covington' under wet conditions. 'Covington' is considered tolerant to wet conditions, though any cultivar will be lost if submerged. 'NC04-0531' will show a proliferation of lenticels under wet conditions.

We claim:

1. A new and distinct cultivar of *Ipomoea batatas* plant named 'NC04-0531', substantially as illustrated and described herein.

* * * * *